(12) United States Patent
Poulsen et al.

(10) Patent No.: US 9,309,295 B1
(45) Date of Patent: Apr. 12, 2016

(54) GENETICALLY MODIFIED FILAMENTOUS FUNGI AND USES THEREOF

(71) Applicant: Danmarks Tekniske Universitet, Kgs.Lyngby (DK)

(72) Inventors: Lars Poulsen, Gentofte (DK); Jette Thykær, Greve (DK); Anna Eliasson Lantz, Helsingborg (SE)

(73) Assignee: Danmarks Tekniske Universitet, Kgs.Lyngby (DK)

( * ) Notice: Subject to any disclaimer, the term of this patent is extended or adjusted under 35 U.S.C. 154(b) by 0 days.

(21) Appl. No.: 14/893,681

(22) PCT Filed: May 28, 2014

(86) PCT No.: PCT/EP2014/061118
§ 371 (c)(1),
(2) Date: Nov. 24, 2015

(87) PCT Pub. No.: WO2014/191487
PCT Pub. Date: Dec. 4, 2014

(30) Foreign Application Priority Data

May 29, 2013 (EP) .................................... 13169726

(51) Int. Cl.
*C12P 21/02* (2006.01)
*C07K 14/37* (2006.01)
*C12P 1/02* (2006.01)

(52) U.S. Cl.
CPC .. *C07K 14/37* (2013.01); *C12P 1/02* (2013.01)

(58) Field of Classification Search
None
See application file for complete search history.

(56) References Cited

U.S. PATENT DOCUMENTS

| 7,338,779 B1 | 3/2008 | Nakari-Setälä et al. | |
| 2006/0106120 A1* | 5/2006 | Abe | B29B 17/00 521/40 |

FOREIGN PATENT DOCUMENTS

WO  WO 01/14521 A1  3/2001

OTHER PUBLICATIONS

Andersen, Mikael R. et al., "Comparative genomics of citric-acid-producing Aspergillus niger ATCC 1015 versus enzyme-producing CBS 513.88" Genome Research, May 4, 2011, pp. 885-897, vol. 21, No. 6.

Dynesen, Jens et al., "Surface Hydrophobicity of Aspergillus nidulans Conidiospores and Its Role in Pellet Formation" Biotechnol., 2003, pp. 1049-1052, vol. 19.

Girardin, H. et al., "The role of the rodlet structure on the physicochemical properties of Aspergillus conidia" Letters in Applied Microbiology, 1999, pp. 364-369, vol. 29.

Jensen, Britt G. et al., "Hydrophobins from Aspergillus species cannot be clearly divided into two classes" BMC Research Notes, 2010, pp. 1-6, vol. 3.

Linder, Markus B. et al., "Hydrophobins: the protein-amphiphiles of filamentous fungi" FEMS Microbiology Reviews, 2005, pp. 877-896, vol. 29.

Nielsen, Michael L. et al., "Efficient PCR-based gene targeting with a recyclable marker for Aspergillus nidulans" Fungal Genetics and Biology, 2006, pp. 54-64, vol. 43.

Pel, Herman J. et al, "Genome sequencing and analysis of the versatile cell factory Aspergillus niger CBS 513.88" Nature Biotechnology, Feb. 2007, pp. 221-231, vol. 25, No. 2.

Veluw, G.J. Van et al., "Heterogeneity in liquid shaken cultures of Aspergillus niger inoculated with melanised conidia or conidia of pigmentation mutants" Studies in Mycology, Sep. 14, 2012, pp. 47-57, vol. 74.

International Search Report for PCT/EP2014/061118 dated Sep. 1, 2014.

\* cited by examiner

*Primary Examiner* — Jim Ketter

(74) *Attorney, Agent, or Firm* — Knobbe Martens Olson & Bear LLP

(57) ABSTRACT

The present invention relates to a filamentous fungus comprising a genetic modification in one more hydrophobin genes and the use of the same as host cell for preparing a biosynthetic product. The present invention further pertains to a vector for and methods for generating said filamentous fungus.

10 Claims, 3 Drawing Sheets

GENETICALLY MODIFIED FILAMENTOUS FUNGI AND USES THEREOF

CROSS REFERENCE TO RELATED APPLICATIONS

This application is a U.S. National Phase Application of PCT International Application Number PCT/EP2014/061118, filed on May 28, 2014, designating the United States of America and published in the English language, which is an International Application of and claims the benefit of priority to European Patent Application No. 13169726.0, filed on May 29, 2013. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SeqList-ZACCO44-005APC.txt, the date of creation of the ASCII text file is Nov. 23, 2015, and the size of the ASCII text file is 8 KB.

FIELD OF THE INVENTION

The present invention relates to a filamentous fungus comprising a genetic modification in one more hydrophobin genes and the use of the same as host cell for preparing a biosynthetic product. The present invention further pertains to a vector for and methods for generating said filamentous fungus.

BACKGROUND OF THE INVENTION

Filamentous fungi are extensively used in fermentation processes in the Biotech industry for production of e.g. enzymes. Growing fungi in a submerged cultivation in reactors often include a substantial mycelia adhesion to the equipment, making the culture heterogeneous. This potentially gives rise to problems as lower productivity and conidia formation as well as a complicated and time consuming cleaning of the equipment. Hydrophobins are proteins forming a hydrophobic coating of both spores and mycelia and these proteins are suspected to be an important cause of the adhesion problem in cultivations with filamentous fungi.

U.S. Pat. No. 7,338,779 relates to submerged fermentation in an aerated and agitated bioreactor and describes methods for reducing foam production in a *Tricoderma* strain by non-selective deleting of every hydrophobin genes of the genome. The hydrophobin deficient *Tricoderma* strain displays less attachment of the cultivation medium to the fermentor surfaces, electrodes, impeller, etc, while the amounts of proteins secreted to the culture medium is increased. U.S. Pat. No. 7,338,779 further suggests that the strategy of deleting the hydrophobin genes may also be applied to *Aspergillus* spp.

A drawback of the above strategy of non-selective deletion of all hydrophobin genes in the cause of reducing the adherence of the fungus to the hardware is that functions of the hydrophobin may have other effects that are detrimental to the fermentation process.

SUMMARY OF THE INVENTION

One object of the present invention is to selectively modify genes encoding hydrophobic proteins expressed on the fungal mycelia and hereby reducing the mycelia adhesion to the surface hence improving the properties the fungi in submerged environments.

More particular, one object of the present invention is provide a improved filamentous fungus with a reduced tendency to adherence of the fungus to the surface and internal hardware and cause foam formation with a minimum impact on the genomic integrity of the fungus.

The present invention provides a solution to the posed problem by selectively targeting the hydrophobin gene, which is differentially higher expressed at pH above 4, such as in the range of pH 4 to 6, for example in the range of pH 4 to 5.

A first aspect of the present invention relates to a filamentous fungus comprising a genetic modification in at least one hydrophobin gene, where said modification reduces or abolishes the activity or expression of said hydrophobin. It is particular preferred not all hydrophobin genes of fungus are genetically modified.

Further, the present invention particular pertains to fungus selected from the genus *Aspergillus* and *Penicillium*. Preferably said fungus comprises a genetic modification in at least two hydrophobin gene, wherein said modifications reduces or abolish the activity or expression of said hydrophobin.

A second aspect of the present invention provides a filamentous fungus comprising a genetic modification in one or more hydrophobins, wherein said fungus comprises at least one transgene.

A third aspect of the present invention pertains to the use of the filamentous fungus of the invention for biosynthesis of a product.

In a further aspect, the present invention relates to a method for preparing a biosynthetic product comprising the steps of:
  (i) providing a filamentous fungus according to the invention, wherein said fungus is further modified to produce said biosynthetic product;
  (ii) culturing the fungus of step (i) under suitable conditions;
  (iii) harvesting said biosynthetic product from the culture of step.

Yet a further aspect of the present invention relates to a vector encoding a hydrophobin gene comprising a modification that reduces or abolishes the activity or expression of said hydrophobin with the proviso that said vector is not adapted for expressing said hydrophobin.

Finally, one aspect of the present invention relates to a method for preparing a filamentous fungus of the invention, said method comprising the steps of:
  (i) providing a filamentous fungus;
  (ii) introducing a genetic modification in at least one hydrophobin gene, which is predominantly expressed above pH 3.5.

BRIEF DESCRIPTION OF THE DRAWINGS AND SEQUENCES

SEQ ID NO: 1—the amino acid sequence of hydrophobin1 (JGI ID 128530; GI:350635529) obtained from *Aspergillus niger*

SEQ ID NO: 2—the coding sequence of the amino acids sequences set forth in SEQ ID NO: 1.

SEQ ID NO: 3—the gene sequence of the amino acids sequences set forth the amino acids sequences set forth in SEQ ID NO: 1. The sequence includes an intron.

SEQ ID NO: 4—a predicted variant of amino acid sequence of hydrophobin1 obtained from *Aspergillus niger.*

SEQ ID NO: 5—the coding sequence of the amino acids sequences set forth in SEQ ID NO: 4.

SEQ ID NO: 6—the gene sequence of the amino acids sequences set forth the amino acids sequences set forth in SEQ ID NO: 4. The sequence includes an intron.

SEQ ID NO: 7—the amino acid sequence of hydrophobin2 (JGI ID 45683; GI:350632707) obtained from *Aspergillus niger*

SEQ ID NO: 8—the coding sequence of the amino acids sequences set forth in SEQ ID NO: 7.

SEQ ID NO: 9—the gene sequence of the amino acids sequences set forth the amino acids sequences set forth in SEQ ID NO: 7. The sequence includes an intron.

FIG. 1 demonstrates the effect of deleting hydrophobin. The flask from a culture of the hydrophobin mutant (right) shows less adhesion than the flask from a culture of the corresponding wild-type.

DETAILED DESCRIPTION OF THE INVENTION

Figure 1:
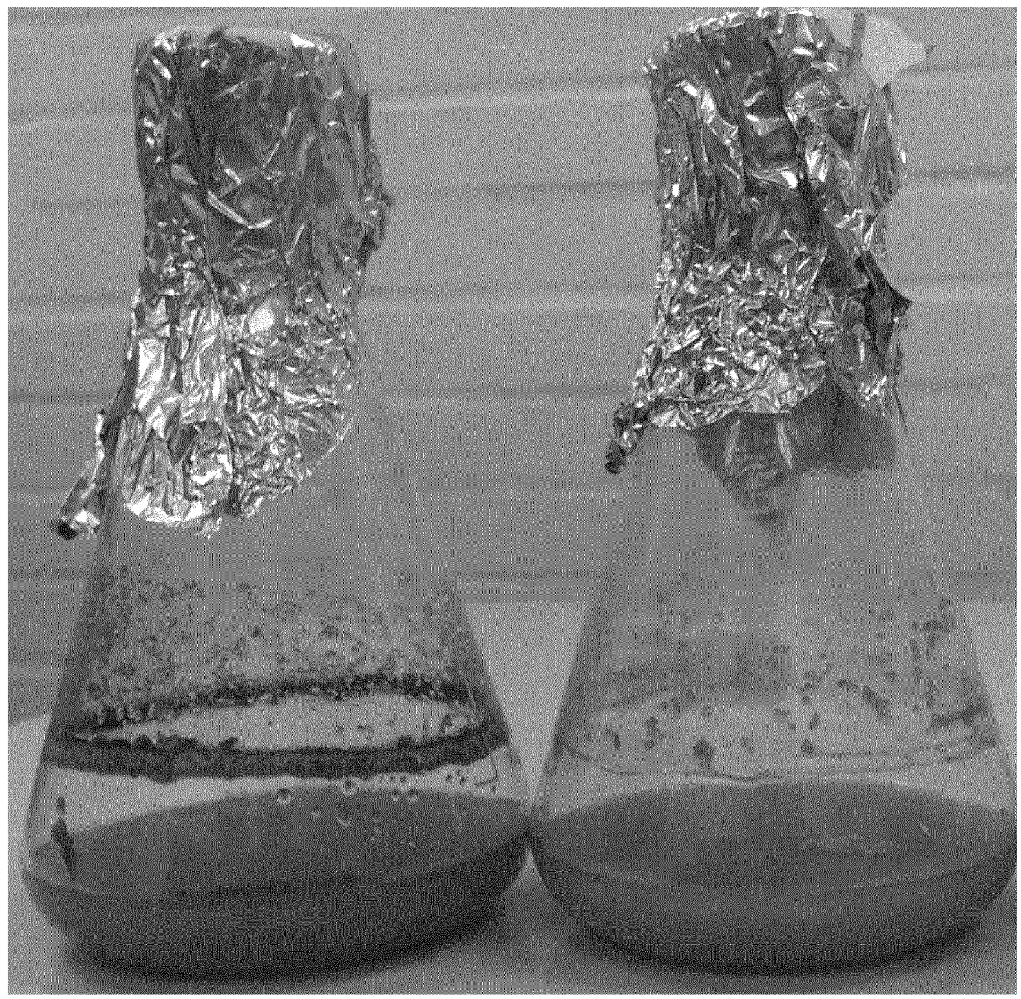

The present invention relates to ways of reducing the tendency of a filamentous fungus adherence to the surface and internal hardware and cause foam formation without otherwise adversely affecting the fermentation process. In particular, the invention relates to the introduction of modifications that reduce or abolish the activity or expression of selected hydrophobin genes in the genome of a filamentous fungus.

Hydrophobins are proteins that form a hydrophobic coating of both spores and mycelia. These proteins are believed to be responsible for the adhesion problem in cultivations with filamentous fungi.

Two classes of hydrophobins, class I and class II, exists and in common are their high efficient function as foam-forming or bubble-nucleating agents. Reducing the concentration of any hydrophobin, in a culture liquid, would therefore result in reduced foam formation.

Hydrophobins have similar physical properties, however the localization and onset of expression varies considerably. Thus these parameters are highly important in regard to mycelia adhesion. To engineering a fungus to become less adhesive, it is important to target the specific hydrophobins. The target hydrophobin should not have an important role in in spore/conidia formation nor germination since both are vital for reproduction and growth for the fungus. Targeting such a hydrophobin might reduce foam formation but significantly impact the spore viability and germination rate consequently leading to grow rate retardation and productivity loss of the hydrophobin mutant.

A hydrophobin which mediates adhesion of the fungus to the surfaces in a bioreactor, expression of the hydrophobin is required to take place in the hyphae. Similarly, the target hydrophobin needs to be expressed under submerged conditions and preferably in the late exponential phase and/or stationary phase. During this phase of the cultivation, mycelia adhesion typically occurs and persist throughout the remaining of the cultivation. Reducing hypae expressed hydrophobins would reduce the adhesion properties of the mycelium. Targeting any other hydrophobins not fulfilling these criteria would in the best cause result in reduced foam formation without significantly reducing mycelia adhesion but more likely also a reduced the fitness of the hydrophobin mutant. Only by targeting careful selected hydrophobins would lead to reduction of mycelia adhesion.

That is, the inventors have found that two of a total of eight hydrophobins in *Aspergillus niger* are upregulated when pH is changed from pH 2 (where *Aspergillus niger* typically produces acids) to pH 4-5 (where *Aspergillus niger* typically produces enzymes). These upregulated hydrophobins result in substantial mycelia adhesion to the equipment as explained above. The corresponding gene encoding the hydrophobin was deleted for one of the hydrophobins that was upregulated, which resulted in less mycelia adhesion thereby completing the invention of reducing the fouling of the bioreactor, and keeping as much of the mycelia available for the submerged fermentation process, thereby increasing the yield from the fermentation.

It was additionally found that the removal of one of the hydrophobins had a beneficial on the morphology of the mycelia, which became more filamentous (larger surface area) instead of pellet like (which has a lower surface area and therefore reduces the access of oxygen needed for the aerobic process).

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Modified Filamentous Fungus

A first aspect of the present invention relates to a filamentous fungus comprising a genetic modification in at least one hydrophobin gene, wherein said modification reduces or abolishes the activity or expression of said hydrophobin.

Different hydrophobins are expressed at different stages of fungal life ranging from vegetative hyphae to sporulating cultures. The function of hydrophobins has been studied by deleting the various hydrophobin genes. The studies demonstrated that the deletion of the individual hydrophobin genes in one way or the other impaired the fungal interacting with the environment. Examples include the formation of aerial structures, essential for spore/conidia formation, as well as growth impaired mutants lacking their hydrophobin covered cell wall (reviewed by Lindler et al, 2005).

In order to avoid introducing modifications which adversely affects the utility of the fungus in a fermentation process, modifications in all or randomly selected hydrophobins genes of the fungus should be avoided. This would cause complications as reduced spore/conidia formation, germination and growth, all essential for inoculum preparation and applying the fungus industrially.

Accordingly, in a preferred embodiment of the present invention, the filamentous fungus comprises a genetic modification in at least one hydrophobin gene, with the proviso that not all hydrophobin genes are genetically modified.

In the context of the present invention, a genetic modification in a hydrophobin gene refers to a modification that reduces the activity or quantity of that hydrophobin in the cell comprising the modification. Thus, the genetic modification in the at least one hydrophobin in the filamentous fungus affects the expression or the activity of the modified hydrophobin. This effect may be accomplished in various ways. The selected hydrophobin gene may be completely or at least partly deleted such that no hydrophobin derived protein is expressed. The modified hydrophobin gene may also be accomplished by partial deletion of the gene and in particular the coding sequence. Similar effect may be obtained by disruption of the gene and in particular the coding sequences, e.g. by insertion of a spacer sequence, e.g. in the form of a marker gene. Finally, the hydrophobin gene may be modified by one or more point mutations.

Thus, in one embodiment of the present invention filamentous fungus comprises a genetic modification in at least one hydrophobin gene, wherein said at least one hydrophobin gene is deleted, partly deleted, disrupted by insertion of a DNA element or mutated in at least one nucleotide position. It follows that the mutation referred to affects the expression of the hydrophobin or the activity of the hydrophobin with regards to tendency of the mycelia adhere to the surface of bioreactors.

In another embodiment, the expression of said at least hydrophobin genes is absent. This may be due to the fact that the gene is deleted or at least disrupted or partially deleted to the extent that no hydrophobin is expressed from the gene. Alternatively, the modification silences the expression of the hydrophobin gene.

The genetically modified hydrophobin may be expressed, but the expression or activity of the hydrophobin should at least be lower than the unmodified counterpart. Thus, where the genetically modified hydrophobin is expressed in the fungus, the overall activity or protein present in the fungus is reduced to a level that significantly reduces the tendency of the fungus to adhere to the surface of and reducing the fouling of the bioreactor. In the context of the present invention the term "activity" refers to the activity of the hydrophobin that confers the adhering properties of the hydrophobin to a surface and thus the fungus to a surface, such as a surface of a bioreactor.

Accordingly, in one embodiment the activity or expression of at one or more hydrophobin genes is significantly reduced compared to the unmodified hydrophobin counterpart. In another embodiment, the activity or expression of said at least one hydrophobin gene is reduced to 50% or less of the activity or the expression of said hydrophobin in said filamentous fungus with no genetic modification. In another embodiment, the activity or expression of said at least one hydrophobin gene is reduced to 40% or less, such as 20% or less, for example 10% or less, such as 5% or less, for example 1% or less than the activity of the unmodified hydrophobin counterpart.

It follows from the above that where the filamentous fungus of the present invention comprises modification in more than one species of hydrophobin genes, such the modifications may have different effect on the species of hydrophobin. For example one modification may completely eliminate the expression of that species of hydrophobin, while the modification of the other species of hydrophobin only reduces activity of that species of hydrophobin in the fungus. Thus, the modifications of the species of hydrophobin are independently selected are thus are not necessarily the same (or have the same effect).

The filamentous fungus of the present invention is not a *Tricoderma* spp. or any strains derived there from. In preferred embodiment, the filamentous fungus is an *Aspergillus* or *Penicillium* species. More preferably, the filamentous fungus is an *Aspergillus* spp. In another preferred embodiment, the *Aspergillus* species selected from the list consisting of *Aspergillus niger, Aspergillus oryzae, Aspergillus terreus*. The filamentous fungus of the present invention includes sub-species of *Aspergillus*, such as *Aspergillus awamori* og *Aspergillus kawachii*.

The inventors has surprisingly discovered that out of a total of eight hydrophobins in *Aspergillus niger*, only two genes are unregulated when the pH of the culture is changed from pH 2 to pH 4-5. The deletion of the two selectively identified hydrophobin genes provides a modified *Aspergillus niger* that displays less mycelia adhesion thereby completing the invention of reducing the fouling of the bioreactor. Further, the morphology of the modified fungus appears to better adapt for an aerobic fermentation process, thereby increasing the yield from the fermentation.

Accordingly, in one embodiment the invention provides a filamentous fungus comprising a genetic modification in at least one hydrophobin gene, wherein said at least one hydrophobin gene encodes a polypeptide comprising an amino acid sequence selected from: SEQ ID #1 (hydrophopin1), an amino acid sequence having at least 85% sequence identity to SEQ ID #1, SEQ ID #7 (hydrophobin2) and an amino acid sequence having at least 85% sequence identity to SEQ ID #7. In a further embodiment the invention, said sequence identity to SEQ ID #1 is at least 90%, such as 95%, for example 96%, 97%, 98% or 99% identical. In yet a further embodiment the invention, said sequence identity to SEQ ID #7 is at least 90%, such as 95%, for example 96%, 97%, 98% or 99% identical.

Hydrophobins contains a characteristic pattern of eight cysteine residues that form four intramolecular disulfide bonds in the pattern Cys1-Cys6, Cys2-Cys5, Cys3-Cys4, Cys7-Cys8 (Kwan et al., 2006). These domains are essential for the hydrophobins function hence modification of amino acids in any of these domains would disrupt the hydrophobin. Thus in one embodiment of the present invention, said at least one hydrophobin gene is genetically modified by deleting, disruption or otherwise mutating the eight cysteine motif of the hydrophobin, e.g. genetically modifying a Cys1-Cys6, Cys2-Cys5, Cys3-Cys4 or Cys7-Cys8 pattern of the hydrophobin gene.

In another embodiment, the invention provides a filamentous fungus comprising a genetic modification in at least one hydrophobin gene, wherein said at least one hydrophobin genes comprises the amino acids sequence set forth in SEQ ID #4 (hydrophopin1 predicted full-length) or an amino acids sequence having at least 85% sequence identity to SEQ ID #4. In one embodiment of the invention, said sequence identity to SEQ ID #4 is at least 90%, such as 95%, for example 96%, 97%, 98% or 99% identical.

In a preferred embodiment, the filamentous fungus comprising a genetic modification in said at least two hydrophobins an *Aspergillus* or *Penicillium* species. More preferably, the filamentous fungus is an *Aspergillus* spp. In another preferred embodiment, the *Aspergillus* species selected from the list consisting of *Aspergillus niger, Aspergillus oryzae, Aspergillus terreus*. The filamentous fungus of the present invention includes sub-species of *Aspergillus*, such as *Aspergillus awamori* og *Aspergillus kawachii*.

In a preferred embodiment, the filamentous fungus comprises a genetic modification in at least one hydrophobin gene that is predominantly expressed in the pH range of 4 to 5 and or upregulated when the pH is changed from pH 2 to pH 4-5. Accordingly, in one embodiment the invention provides a filamentous fungus comprising a genetic modification in at least one hydrophobin gene that is predominantly expressed in the pH range of 4 to 5 and or upregulated when the pH is changed from pH 2 to pH 4-5. The term predominantly refers to the predominant expression of the species hydrophobin compared to the average expression of the total number of species of hydrophobins in the fungus.

In a more preferred embodiment, the filamentous fungus of the present invention comprises a genetic modification in at least two hydrophobin genes, wherein said modifications reduces or abolish the activity or expression of said hydrophobin. In the most preferred embodiment, one of said two hydrophobin gene is a nucleic acid sequence encoding SEQ ID #1 (hydrophopin1), a nucleic acid sequence encoding an amino acids sequence having at least 85% sequence identity to SEQ ID #1 and the second of said two hydrophobin gene is a nucleic acid sequence encoding SEQ ID #7 (hydrophobin2) or a nucleic acid sequence encoding an amino acids sequence having at least 85% sequence identity to SEQ ID #7. In a further embodiment of the invention, said sequence identity to SEQ ID #1 is at least 90%, such as 95%, for example 96%, 97%, 98% or 99% identical. In yet a further embodiment the invention, said sequence identity to SEQ ID #7 is at least 90%, such as 95%, for example 96%, 97%, 98% or 99% identical.

Sequence Identity

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $(N_{ref} - N_{dif}) \times 100 / N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

With respect all embodiments of the invention relating to nucleotide sequences, the percentage of sequence identity between one or more sequences may also be based on alignments using any suitable software such as the clustalW software (http:/www.ebi.ac.uk/clustalW/index.html) with default settings. For nucleotide sequence alignments these settings are: Alignment=3Dfulll Gap Open 10.00, Gap Ext. 0.20, Gap separation Dist. 4, DNA weight matrix: identity (IUB).

Alternatively, nucleotide sequences also may be analysed using any suitable software such as DNASIS Max and the comparison of the sequences may be done at http://www-.paraliqn.orq/. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method are published in Rognes (2001).

When referring to complementary sequences, the following base pairing rules can be applied, G pairs to C and U, A pairs to T and U. "Nucleic acids sequence" and "polynucleotide sequence" are interchangeable terms in the context of the present invention.

Host Cell

As mentioned herein, one object of the present invention is to selectively modify genes encoding hydrophobins expressed on the fungal mycelia and hereby reducing the mycelia adhesion to the surface hence improving the properties the fungi in submerged environments. It follows that the filamentous fungus of the present invention may be used as host cell (producer cell) for the (recombinant) production of a biosynthetic product, such as a peptide, polypeptide/protein, a lipid, a (poly)saccharide, a nucleoside, an enzyme, an antibiotic, a biosynthetical drug, or a metabolite. The host cell/producer cell is typically established by the introduction of a transgene, typically in the form of an expression vector encoded and adapted for expression of typically a protein or peptide in the hosting filamentous fungus. Alternatively, the object may be to produce a biosynthetic product, which require the introduction of a one or more genes encoding the products require for establishing a biosynthetic pathway for producing a biosynthetic product of interest. Example of such biosynthetic product is mycophenolic acid. A cluster of eight genes are involved in the biosynthesis of mycophenolic acid (Regueira et al., 2011). Accordingly, a biosynthetic pathway for production of a biosynthetic product such as mycophenolic acid may be established by introducing and expressing the essential cluster of genes in the filamentous fungus of the present invention. The filamentous fungus thereby becomes producer cell of the biosynthetic product, e.g. mycophenolic acid.

One aspect of the present invention therefore relates to a filamentous fungus comprising a genetic modification in at least one hydrophobin gene, where said modification reduces or abolishes the activity or expression of said hydrophobin,
  wherein said fungus is *Aspergillus* spp and with the proviso that not all hydrophobin genes of said fungus are genetically modified, and
  wherein said fungus further comprises at least one transgene, wherein said transgene is encoded by an expression vector adapted for expression of said transgene in said fungus.

As mentioned herein, the term "activity" refers to the activity of the hydrophobin that confers the adhering properties of the hydrophobin to a surface and thus the fungus to a surface, such as a surface of a bioreactor. Thus, the term "activity" refers the biophysical properties of the hydrophobin, i.e. the surface activity of the hydrophobin. In the context of the present invention the filamentous fungus, such as a *Aspergillus* spp of the present invention, comprises a genetic modification in at least one hydrophobin gene that reduces or abolishes the surface activity of said hydrophobin relative to the wildtype hydrophobin.

The filamentous fungus comprising a genetic modification in at least one hydrophobin gene and said at least one transgene is referred to as a "host cells" or "producer cell". A host cell of the present invention may thus be prepared by introducing a transgene in a filamentous fungus of the present invention, wherein said transgene is encoded by an expression vector adapted for expression in said fungus. The vector may be present in the host cell as a episomal vector or the vector may be stably integrated in the genome of the host. It follows that in the context of the present invention a *Aspergillus* spp host cells is a *Aspergillus* spp of the invention comprising a genetic modification in at least one hydrophobin gene and further comprising an expression vector, wherein said an expression vector comprises a transgene operatively linking a promoter adapted for expression in said fungus The above host cell based on the *Aspergillus* spp having a genetic modification in at least one hydrophobin gene may be used for heterologous production (biosynthesis) of a biosynthetic product such as an amino acid, fatty acid, and metabolites and other natural products or precursors of these entities. The biosynthetic product also covers peptides, proteins, enzymes, vitamins, lipids, (poly)saccharides, nucleosides, biosynthetical drugs and antibiotics. In a preferred embodiment, transgene encodes a protein, which is expressed in the host cell from which is may be harvested or the culturing media in the case the protein is secreted from the host cell.

A preferred embodiment of the present invention relates to a filamentous fungus comprising a genetic modification in at least one hydrophobin gene,
  wherein said at least one hydrophobin genes encodes a polypeptide comprising an amino acid sequence selected from the list consisting of: the amino acid sequence having the sequence set forth in SEQ ID #1, an amino acid sequence having at least 85% sequence identity to SEQ ID #1, the amino acid sequence having the sequence set forth in SEQ ID #7, an amino acid sequence having at least 85% sequence identity to SEQ ID #7, the amino acid sequence set forth in SEQ ID #4 and an amino acid sequence having at least 85% sequence identity to SEQ ID #4 wherein said modification reduces or abolishes the activity or expression of said hydrophobin, wherein said fungus is *Aspergillus* spp and with the proviso that not all hydrophobin genes of said fungus are genetically modified, and wherein said fungus further comprises at least one transgene, wherein said transgene is encoded by an expression vector adapted for expression of said transgene.

Another embodiment relates to a filamentous fungus comprising a genetic modification in at least one hydrophobin gene, wherein said at least one hydrophobin genes encodes a polypeptide comprising an amino acid sequence having the sequence set forth in SEQ ID #1 or an amino acid sequence having at least 85% sequence identity to SEQ ID #1, wherein said modification reduces or abolishes the activity or expression of said hydrophobin, wherein said fungus is *Aspergillus* spp and with the proviso that not all hydrophobin genes of said fungus are genetically modified, and wherein said fungus further comprises at least one transgene, wherein said transgene is encoded by an expression vector adapted for expression of said transgene.

Another embodiment relates to a filamentous fungus comprising a genetic modification in at least one hydrophobin gene, wherein said at least one hydrophobin genes encodes a polypeptide comprising an amino acid sequence having the sequence set forth in SEQ ID #7 or an amino acid sequence having at least 85% sequence identity to SEQ ID #7, wherein said modification reduces or abolishes the activity or expression of said hydrophobin, wherein said fungus is *Aspergillus* spp and with the proviso that not all hydrophobin genes of said fungus are genetically modified, and wherein said fungus further comprises at least one transgene, wherein said transgene is encoded by an expression vector adapted for expression of said transgene.

One embodiment relates to a filamentous fungus comprising a genetic modification in at least one hydrophobin gene, wherein said at least one hydrophobin genes encodes a polypeptide comprising an amino acid sequence having the sequence set forth in SEQ ID #4 or an amino acid sequence having at least 85% sequence identity to SEQ ID #4, wherein said modification reduces or abolishes the activity or expression of said hydrophobin, wherein said fungus is *Aspergillus* spp and with the proviso that not all hydrophobin genes of said fungus are genetically modified, and wherein said fungus further comprises at least one transgene, wherein said transgene is encoded by an expression vector adapted for expression of said transgene.

In yet another embodiment relates to a filamentous fungus comprising a genetic modification in one and no more than one hydrophobin gene, wherein said at least one hydrophobin genes encodes a polypeptide comprising an amino acid sequence having the sequence set forth in SEQ ID #1 or an amino acid sequence having at least 85% sequence identity to SEQ ID #1, wherein said modification reduces or abolishes the activity or expression of said hydrophobin, wherein said fungus is *Aspergillus* spp, and wherein said fungus further comprises at least one transgene, wherein said transgene is encoded by an expression vector adapted for expression of said transgene.

A further embodiment relates to a filamentous fungus comprising a genetic modification in one and no more than one hydrophobin gene, wherein said at least one hydrophobin genes encodes a polypeptide comprising an amino acid sequence having the sequence set forth in SEQ ID #7 or an amino acid sequence having at least 85% sequence identity to SEQ ID #7, wherein said modification reduces or abolishes the activity or expression of said hydrophobin, wherein said fungus is *Aspergillus* spp, and wherein said fungus further comprises at least one transgene, wherein said transgene is encoded by an expression vector adapted for expression of said transgene.

One embodiment relates to a filamentous fungus comprising a genetic modification in one and no more than one hydrophobin gene, wherein said at least one hydrophobin genes encodes a polypeptide comprising an amino acid sequence having the sequence set forth in SEQ ID #4 or an amino acid sequence having at least 85% sequence identity to SEQ ID #4, wherein said modification reduces or abolishes the activity or expression of said hydrophobin, wherein said fungus is *Aspergillus* spp, and wherein said fungus further comprises at least one transgene, wherein said transgene is encoded by an expression vector adapted for expression of said transgene.

The present invention further provides an *Aspergillus* spp host cell having a genetic modification in two hydrophobins, e.g. in SEQ ID #1 or SEQ ID #4 in combination with SEQ ID #7.

Accordingly, one embodiment of the present invention relates to a filamentous fungus comprising a genetic modification in two hydrophobin genes, wherein the first hydrophobin genes encodes a polypeptide comprising an amino acid sequence having the sequence set forth in SEQ ID #1 or an amino acid sequence having at least 85% sequence identity to SEQ ID #1, wherein said at least one hydrophobin genes encodes a polypeptide comprising an amino acid sequence having the sequence set forth in SEQ ID #7 or an amino acid sequence having at least 85% sequence identity to SEQ ID #7, wherein said modification reduces or abolishes the activity or expression of said hydrophobin, wherein said fungus is *Aspergillus* spp and with the proviso that not all hydrophobin genes of said fungus are genetically modified, and wherein said fungus further comprises at least one transgene, wherein said transgene is encoded by an expression vector adapted for expression of said transgene.

In one embodiment, the at least one hydrophobin gene is deleted, partly deleted, disrupted by insertion of a DNA element or mutated in at least one nucleotide position. In another embodiment, the expression of said at least one hydrophobin gene is absent or, wherein the activity or expression of said at least one hydrophobin gene is reduced to 50% or less of the activity or the expression of said hydrophobin in said filamentous fungus with no genetic modification.

In yet an embodiment of the present invention said fungus (host cell) is an *Aspergillus* species selected from the list consisting of *Aspergillus niger, Aspergillus oryzae, Aspergillus terreus*. The host cell of the present invention includes sub-species of *Aspergillus*, such as *Aspergillus awamori* og *Aspergillus kawachii*.

In a preferred embodiment said at least one hydrophobin gene encodes a polypeptide comprising an amino acid sequence selected from: SEQ ID #1, an amino acid sequence having at least 85% sequence identity to SEQ ID #1, SEQ ID #7 and an amino acid sequence having at least 85% sequence identity to SEQ ID #7.

In a preferred embodiment, the filamentous fungus according to any of the preceding claims, wherein said at least one hydrophobin gene comprises the amino acid sequence set forth in SEQ ID #4 or an amino acid sequence having at least 85% sequence identity to SEQ ID #4.

In one embodiment, the filamentous fungus comprises said at least one transgene comprising a genetic modification in at least two hydrophobin genes, wherein said modifications reduces or abolishes the activity or expression of said hydrophobins. In a preferred embodiment, one of said two hydrophobin genes is a sequence encoding SEQ ID #1, an amino acid sequence having at least 85% sequence identity to SEQ ID #1 and the second of said two hydrophobin gene is a sequence encoding SEQ ID #7 or an amino acid sequence having at least 85% sequence identity to SEQ ID #7.

In a further embodiment of the host cells of the present invention, said sequence identity to SEQ ID #1 is at least 90%, such as 95%, for example 96%, 97%, 98% or 99% identical. In yet a further embodiment of the host cells of the present invention, said sequence identity to SEQ ID #7 is at least 90%, such as 95%, for example 96%, 97%, 98% or 99% identical.

In a preferred embodiment, the *Aspergillus* spp host cell of the present invention comprises a genetic modification in at least one hydrophobin gene that is predominantly expressed in the pH range of 4 to 5 and or upregulated when the pH is changed from pH 2 to pH 4-5. Accordingly, in one embodiment the invention provides a *Aspergillus* spp host cell comprising a genetic modification in at least one hydrophobin gene that is predominantly expressed in the pH range of 4 to 5 and or upregulated when the pH is changed from pH 2 to pH 4-5.

Accordingly, in one embodiment of the filamentous fungus of the present invention further comprises at least one transgene. In a further embodiment, the filamentous fungus comprises at least two, such as at least three, for example at least four, such as at least five, for example at least six, such as at least seven, for example at eight six transgenes.

Definition of Transgene

In the context of the present invention, the term "transgene" refers to genetic material, preferable in the form of DNA, which has been introduced in an organism. Typically, the "transgene" is obtained from heterologous organism and thus the transgene is referred to as heterologous genetic material, such as a heterologous DNA sequence. Ways of introducing genetic material into an organism such as a filamentous fungus are many and well know to the person skilled in the art.

The transgene is typically provided in the form of an expression vector comprising the transgene and adapted for expression of products encoded by the transgene.

The term "vector" refers to a DNA molecule used as a vehicle to transfer recombinant genetic material into a host cell. Examples of vectors are plasmids, cosmids, and artifical chromosomes. The vector itself is generally a DNA sequence that consists of an insert (a transgene, a heterologous nucleic acid sequence) and a larger sequence that serves as the "backbone" of the vector. The purpose of a vector which transfers genetic information to the host is typically to isolate, multiply, or express the insert in the target cell. Vectors called "expression vectors" (expression constructs) are specifically adapted for the expression of the heterologous sequences in the target cell (i.e. the filamentous fungus of the present invention), and generally have a promoter sequence that drives expression of the heterologous sequences. The choice of vector employed in embodiments of the present invention depends on the specific application of the vector encoding the polypeptides or polynucleotide of the invention.

Operatively Linked

The term "operatively linked" refers to the connection of elements being a part of a functional unit such as a gene or an open reading frame. Accordingly, by operatively linking a promoter to a nucleic acid sequence encoding a polypeptide the two elements becomes part of the functional unit—a gene. The linking of the expression control sequence (promoter) to the nucleic acid sequence enables the transcription of the nucleic acid sequence directed by the promoter. By operatively linking two heterologous nucleic acid sequences encoding a polypeptide the sequences becomes part of the functional unit—an open reading frame encoding a fusion protein comprising the amino acid sequences encoding by the heterologous nucleic acid sequences. By operatively linking two amino acids sequences, the sequences become part of the same functional unit—a polypeptide. Operatively linking two heterologous amino acid sequences generates a hybrid (fusion) polypeptide.

Where more than one transgene is introduced in the filamentous fungus, they may be introduced in the form of one or more expression vector comprising and adapted for expression of more than one transgene. Thus, an expression vector may comprise and be adapted for expression of more than one species of transgenes. Alternatively, the transgenes are inserted in separate expression vectors an introduced in the filamentous fungus accordingly.

Accordingly, in one embodiment the filamentous fungus, the transgene is encoded by an expression vector adapted for expression of said transgene. As mentioned, the product encoded by the transgene and expressed from the vector may be a protein. Where more than one transgene is introduced, these transgene may collectively encode the biosynthesis of a product, e.g. a metabolite. In a preferred embodiment, the transgene encodes a protein, polypeptide or peptide. In a preferred embodiment, the expression vector adapted for expression of said transgene is a plasmid vector, where the expression is adapted for expression in a filamentous fungus.

The filamentous fungus of the invention further comprising at least one transgene, e.g. provided in the form of an expression vector, may thus be used a host cell or producer cell for production of a product encoded by the expression vector.

Method of Producing a Biosynthetic Product

One aspect of the invention relates to the use of the filamentous fungus of the invention for biosynthesis of a product.

A further aspect relates to a method for preparing a biosynthetic product comprising the steps of:
 (i) providing a filamentous fungus of the present invention, wherein said fungus is further modified to produce said biosynthetic product;

(ii) culturing the fungus of step (i) under suitable conditions;
(iii) harvesting said biosynthetic product from the culture of step.

The biosynthetic product may be an amino acid, fatty acid, and metabolites and other natural products or precursors of these entities. The biosynthetic product also covers peptides, proteins, vitamins, enzymes, lipids, (poly)saccharides, nucleosides, biosynthetical drugs and antibiotics. Biosynthetic products such as carnitine, cholesterol and many others are built in biosynthetic pathways and thus requires that the transgenes required for the biosynthetic pathway is expressed in the filamentous fungus used by the method. In one embodiment, the biosynthetic product is a metabolite. In a preferred embodiment, the biosynthetic product is a protein or an enzyme. The art of culturing a filamentous fungus, such as *Aspergillus* or *Penicillium* species, as producers of a biosynthetic product is well known in the art and falls within the capacity of the skilled person.

In one embodiment of the present invention, the filamentous fungus used by the method is a species of *Aspergillus* or *Penicillium*. In another particular preferred embodiment, the fungus is an *Aspergillus* spp, such as *Aspergillus* species selected from the list consisting of *Aspergillus niger, Aspergillus oryzae, Aspergillus terreus*, including sub-species of *Aspergillus*, such as *Aspergillus awamori* og *Aspergillus kawachii*. More preferably, the filamentous provided in step (i) is one of the *Aspergillus* spp host cells mentioned in the section "Host cell".

Targeting Vector

In the context of the present invention, the term "targeting vector" refers to the vector used for the introduction of the genetic modification in a selected hydrophobin gene of the filamentous fungus. Since the object is not to introduce the vector for expression purpose, it follows that the vector is preferably not adapted for expression of the hydrophobin or fragment thereof encoded by the targeting vector.

The purpose of the targeting vector is to introduce modifications in the selected endogenous hydrophobin such that the modification abolishes the expression of or at least reduces the activity of the hydrophobin encoded by the modified hydrophobin gene. Thus, the targeting vector or parts thereof is inserted into the genome of the filamentous fungus, and disables (or partly disables) the selected hydrophobin (the target gene).

Accordingly, one aspect of the present invention provides a targeting vector encoding a hydrophobin gene comprising a modification that reduces or abolishes the activity or expression of said hydrophobin with the proviso that said vector is not adapted for expressing said hydrophobin.

There are a large number of various designs of targeting vectors. Generally, the vector needs to be introduced in a linearized form and where the targeting vector is circular, the linearization must occur outside of the arms of homology, so provision must be made for a unique recognition sequence for linearization, e.g. by a restriction enzyme at an appropriate place. Further, a strategy for detection of a filamentous fungus comprising the desired genetic modification involves some sort of means for screening, for example a unique genetic marker, which may be selected for or detected by DNA hybridization or PCR amplification. Finally, the greater the amount of sequence match, the more likely the targeting is to succeed.

In one embodiment of the present invention, the targeting vector is a polynucleotide, preferably in linear form comprising a marker sequence (such as a selectable marker) flanked on both sides by targeting sequences, i.e. hydrophobin gene or fragment. The marker sequence may be pyr-4, amdS, hygromycin resistance or Bleomycin resistance. The targeting vector may be provided in the form of a linearized plasmid vector. In another preferred embodiment, the targeting vector is provided in the form of a linear PCR product. Examples of such targeting vector design and application of the same is disclosed in Nielsen et al. (2005).

In one embodiment of the present invention, the targeting vector comprises a nucleic acid sequence encoding a hydrophobin gene that encodes a polypeptide comprising an amino acids sequence selected from: SEQ ID #1 (hydrophopin1), an amino acid sequence having at least 85% sequence identity to SEQ ID #1, SEQ ID #7 (hydrophobin2) and an amino acid sequence having at least 85% sequence identity to SEQ ID #7. In a further embodiment of the invention, said sequence identity to SEQ ID #1 is at least 90%, such as 95%, for example 96%, 97%, 98% or 99% identical. In yet a further embodiment the invention, said sequence identity to SEQ ID #7 is at least 90%, such as 95%, for example 96%, 97%, 98% or 99% identical. The targeting vector may encode the entire sequence of the hydrophobin, which may separate in parts, e.g. flanking a marker sequence. Alternatively, the targeting vector may encode a part of the hydrophobin sequence.

The purpose of the application of the targeting vector is to introduce modification in the selected hydrophobin gene such that the modification abolishes the expression of or at least reduces the activity of the hydrophobin encoded by the modified hydrophobin gene. In one embodiment, the targeting vector therefore comprises a hydrophobin gene that comprises a deletion, disrupted by insertion of a DNA element or mutated in at least one nucleotide position. Alternatively, the targeting vector is designed in such a way that the targeted integration of the vector in the selected hydrophobin gene introduced the genetic modification that abolishes the expression of or at least reduces the activity of the hydrophobin encoded by the modified hydrophobin gene.

Method of Making a Modified Filamentous Fungus

The making of the filamentous fungus of the present invention rely in prior identification of at least one preferably more hydrophobins that predominantly contribute to the mycelia adhesion to the bioreactor and thus the fouling of the same. More particular, the making of the filamentous fungus of the present rely on the prior identification of species of hydrophobins, which are predominantly expressed in the pH range of 4 to 5 and or upregulated when the pH is changed from pH 2 to pH 4-5. Most preferably only such species are modified.

Accordingly, one aspect of the present invention relates to a method for preparing a filamentous fungus according to of the invention, said method comprising the steps of:
(i) providing a filamentous fungus;
(ii) introducing a genetic modification in at least one hydrophobin gene, which is predominantly expressed above pH 3.5.

In a preferred embodiment, the at least one hydrophobin genes is predominantly expressed in the pH range from 4 to 6, preferably in the pH range from 4 to 5.

In a more preferred embodiment, a genetic modification is introduced in at least two hydrophobin genes. Preferably both of hydrophobin genes are predominantly expressed at pH above pH 3.5 such as in the pH range from 4 to 5. In another preferred embodiment, the filamentous fungus is an *Aspergillus* or *Penicillium* species.

In a further embodiment, said at least one hydrophobin gene encodes a polypeptide comprising an amino acid sequence selected from: SEQ ID #1 (hydrophopin1), an amino acid sequence having at least 85% sequence identity to SEQ ID #1, SEQ ID #7 (hydrophobin2) and an amino acid sequence having at least 85% sequence identity to SEQ ID #7. In a further embodiment of the invention, said sequence identity to SEQ ID #1 is at least 90%, such as 95%, for example 96%, 97%, 98% or 99% identical. In yet a further embodiment the invention, said sequence identity to SEQ ID #7 is at least 90%, such as 95%, for example 96%, 97%, 98% or 99% identical. In another embodiment, said at least one hydrophobin genes comprises the amino acid sequence set forth in SEQ ID #4 (hydrophopin1 predicted full-length) or an amino acid sequence having at least 85% sequence identity to SEQ ID #4. In one embodiment of the invention, said sequence identity to SEQ ID #4 is at least 90%, such as 95%, for example 96%, 97%, 98% or 99% identical.

In yet a further embodiment, a genetic modification is introduced in a hydrophobin genes that encodes a polypeptide comprising an amino acid sequence selected from: SEQ ID #1 (hydrophopin1), an amino acid sequence having at least 85% sequence identity to SEQ ID #1 and a further modification in a hydrophobin genes that encodes a polypeptide comprising an amino acid sequence selected from: SEQ ID #7 (hydrophobin2) and an amino acid sequence having at least 85% sequence identity to SEQ ID #7. In a further embodiment of the invention, said sequence identity to SEQ ID #1 is at least 90%, such as 95%, for example 96%, 97%, 98% or 99% identical. In yet a further embodiment the invention, said sequence identity to SEQ ID #7 is at least 90%, such as 95%, for example 96%, 97%, 98% or 99% identical.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The term "comprising", "comprise" and "comprises" herein are intended by the inventors to be optionally substitutable with the tern "consisting of", consist of and "consists of", respectively, in every instance.

The invention will hereinafter be described by way of the following non-limiting items.

Item 1. A filamentous fungus comprising a genetic modification in at least one hydrophobin gene, where said modification reduces or abolishes the activity or expression of said hydrophobin.

Item 2. The filamentous fungus of item 1 with the proviso that not all hydrophobin genes are genetically modified.

Item 3. The filamentous fungus of item 1 or 2, wherein said at least one hydrophobin gene is deleted, partly deleted, disrupted by insertion of a DNA element or mutated in at least one nucleotide position.

Item 4. The filamentous fungus according to any of the preceding items, wherein expression of said at least hydrophobin gene is absent.

Item 5. The filamentous fungus according to any of the preceding items, wherein the activity or expression of said at least one hydrophobin gene is reduced to 50% or less of the activity or the expression of said hydrophobin in said filamentous fungus with no genetic modification.

Item 6. The filamentous fungus according to any of the preceding items, wherein said fungus is an *Aspergillus* or *Penicillium* species.

Item 7. The filamentous fungus according to any of the preceding items, wherein said fungus is an *Aspergillus* spp.

Item 8. The filamentous fungus of item 7, wherein said fungus is an *Aspergillus* species selected from the list consisting of *Aspergillus niger*, *Aspergillus oryzae*, and *Aspergillus terreus*.

Item 9. The filamentous fungus according to any of the preceding items, wherein said at least hydrophobin gene encodes a polypeptide comprising an amino acid sequence selected from: SEQ ID #1 (hydrophopin1), an amino acid sequence having at least 85% sequence identity to SEQ ID #1, SEQ ID #7 (hydrophobin2) and an amino acid sequence having at least 85% sequence identity to SEQ ID #7.

Item 10. The filamentous fungus according to any of the preceding items, wherein said at least one hydrophobin gene comprises the amino acid sequence set forth in SEQ ID #4 (hydrophopin1 predicted full-length) or an amino acids sequence having at least 85% sequence identity to SEQ ID #4.

Item 11. The filamentous fungus according to any of the preceding items comprising a genetic modification in at least two hydrophobin genes, wherein said modifications reduce or abolish the activity or expression of said hydrophobin.

Item 12. The filamentous fungus according to item 11, wherein one of said two hydrophobin gene is a sequence encoding SEQ ID #1 (hydrophopin1), an amino acid sequence having at least 85% sequence identity to SEQ ID #1 and the second of said two hydrophobin gene is an amino acid sequence encoding SEQ ID #7 (hydrophobin2) or an amino acids sequence having at least 85% sequence identity to SEQ ID #7.

Item 13. The filamentous fungus according to any of the preceding items, wherein said fungus further comprises at least one transgene.

Item 14. The filamentous fungus according to item 13, wherein said transgene is encoded by an expression vector adapted for expression of said transgene.

Item 15. The filamentous fungus according to item 13 or 14, wherein said transgene encodes a protein.

Item 16. Use of the filamentous fungus according to any of the preceding items for biosynthesis of a product.

Item 17. A method for preparing a biosynthetic product comprising the steps of:
(i) providing a filamentous fungus according to any of the preceding items, wherein said fungus is further modified to produce said biosynthetic product;
(ii) culturing the fungus of step (i) under suitable conditions;
(iii) harvesting said biosynthetic product from the culture of step (ii).

Item 18. The method of item 17, wherein said product is selected from the list consisting of a protein or a metabolite.

Item 19. A targeting vector encoding a hydrophobin gene comprising a modification that reduces or abolishes the activity or expression of said hydrophobin with the proviso that said vector is not adapted for expressing said hydrophobin.

Item 20. The targeting vector of item 19, wherein said the hydrophobin gene encodes a polypeptide comprising an amino acid sequence selected from: SEQ ID #1 (hydrophopin1), an amino acid sequence having at least 85% sequence identity to SEQ ID #1, SEQ ID #7 (hydrophobin2) and an amino acid sequence having at least 85% sequence identity to SEQ ID #7.

Item 21. The targeting vector of item according to item 19 or 20, wherein said hydrophobin gene comprises a deletion, disrupted by insertion of a DNA element or mutated in at least one nucleotide position.

Item 22. A method for preparing a filamentous fungus according to any of the preceding items, said method comprising the steps of:
(i) providing a filamentous fungus;
(ii) introducing a genetic modification in at least one hydrophobin genes, which are predominantly expressed above pH 3.5.

Item 23. The method for preparing a filamentous fungus according to item 22, wherein the least one hydrophobin genes is predominantly expressed in the pH range from 4 to 5.

Item 24. The method for preparing a filamentous fungus according to item 22 or 23, wherein a genetic modification is introduced in at least two hydrophobin genes.

Item 25. The method for preparing a filamentous fungus according to any of the preceding items, wherein the filamentous fungus is an *Aspergillus* or *Penicillium* species.

The invention will hereinafter be described by way of the following non-limiting Examples.

EXAMPLES

Example 1

Target Selection and Gene Deletion

Transcriptional data of biomass obtained from chemostat cultivations of a transcription factor mutant and wild type strain at two different pH conditions (pH 2.5 and 5.0) was analyzed, using ANOVA statistical testing, to determine genes subjected to differential transcriptional regulation. The regulatory effect of the pH was isolated and fold change ratio (LOG 2) was calculated. Empiric Bayesian statistics were used to moderate the standard errors within each gene, and Benjamini-Hochberg's method, to adjust for multitesting. A cut-off value of adjusted $P<0.05$ was set to assess statistical significance A summary of the data are found in table 1.

TABLE 1

Significantly expressed hydrophobins.

| JGI ID | Fold change, pH | Adj. P value |
|---|---|---|
| 128530 | 4.472 | 1.14E-05 |
| 53462 | -4.922 | 2.86E-05 |
| 45683 | 3.501 | 0.0047 |
| 45685 | 1.182 | 0.0074 |
| 43184 | 1.788 | 0.0257 |

From table 1, it is clear that hydrophobin 128530 and 45683 are progressively reacting to increasing pH. This response is likewise seen when observing mycelia adhesion in bioreactors. At low pH (pH below 3), mycelia adhesion of *A. niger* is absent/vague whereas at a pH value above 4 mycelia adhesion become apparent and predominant issue. The combination of the two pH responding hydrophobins with mycelia adhesion being predominant at high pH, was the foundation for the discovery and formed basis for the gene deletion.

Example 2

As gene deletion strategy, a bipartite gene knockout method was selected (Nielsen et al. 2006). The knockout substrate consisted of two-parts; one, contained a fragment upstream of the gene, fused to a truncate hygromycin marker (2/3 the marker gene, lacking the end). The second part contained a truncate hygromycin marker (2/3 the marker gene, lacking the start) fused to a fragment, downstream to of the gene. The knockout substrate was amplified individually by PCR and transformed into in *A. niger* by standard protoplast/PEG mediated transformation. The gene deletion was achieved by insertion of the substrate into *A. niger*'s genome by means of homologous recombination.

Example 3

The gene deletion was verified using PCR and tested for ectopic insertions by Southern analysis.

The mutant strain (delta 128530) was initially investigated in 500 mL shake flaks, without baffels. The flasks were filled with 100 mL of watman medium and inoculated to a final spore concentration of 2E09 spores/L, the agitation speed was 150 RPM and the temperature was controlled to 30° C. After 4 days photos were taken of the flasks, see FIG. 1.

Figure 2:
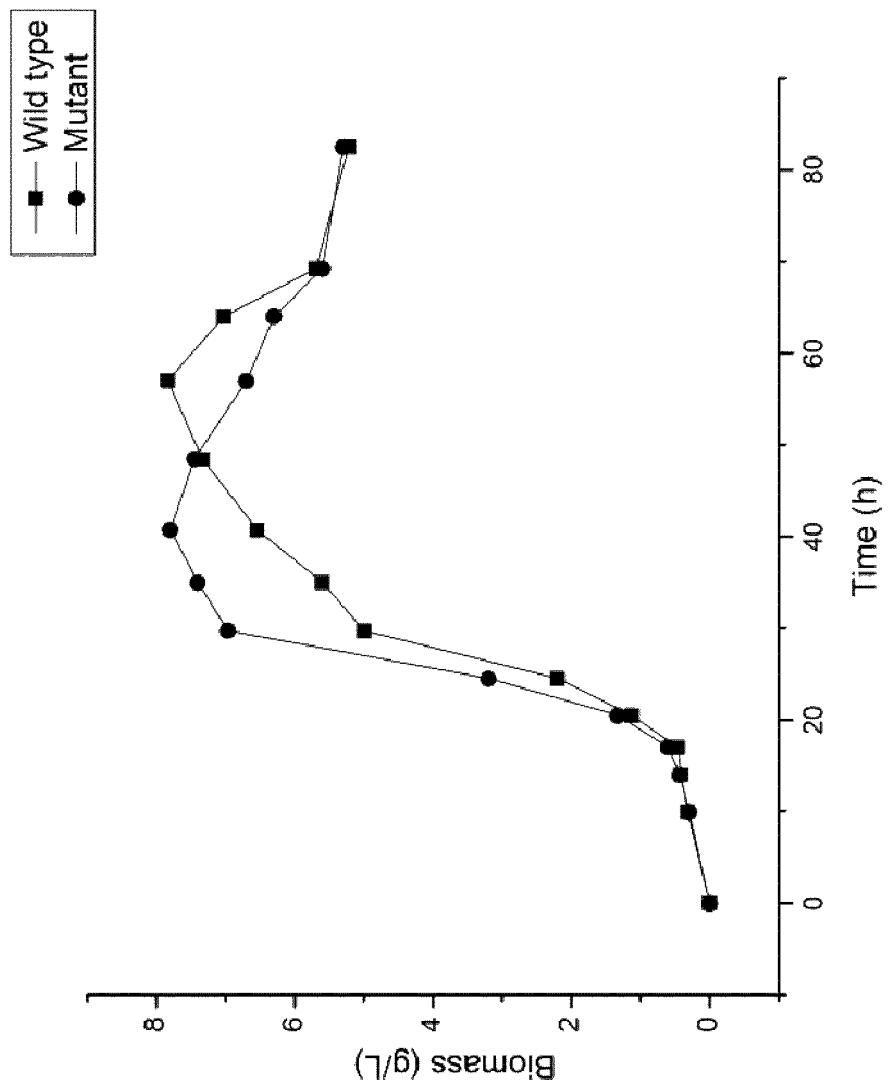
FIG. 2 shows profiles of the biomass concentration during batch cultivations at pH 5.0 with the WT-strain and the Δ128530 mutant strain.

Further investigation of the mutant was done in a 2 L Sartorius bioreactor with a working volume of 1.8 L. The temperature was maintained at 30° C. during the cultivation and pH was controlled by automatic addition of 2 M NaOH and 1 M HCl. Initial conditions in the bioreactor were pH: 3.0; stirring rate: 100 rpm; and aeration: 0.2 volumes of air per volume of fluid per minute (vvm). After germination, the stirring rate was gradually increased to 800 rpm and the air flow to 1 vvm. The pH was adjusted to 5.0 with addition of 2 M NaOH or 1 M HCl over 2 hours. The bioreactor was sampled during the cultivation. The cell mass concentration on a dry weight basis was determined by the use of nitrocellulose filters with a pore size of 0.45 µm. Representative profiles of the biomass concentration can be found in FIG. 2.

Figure 3:
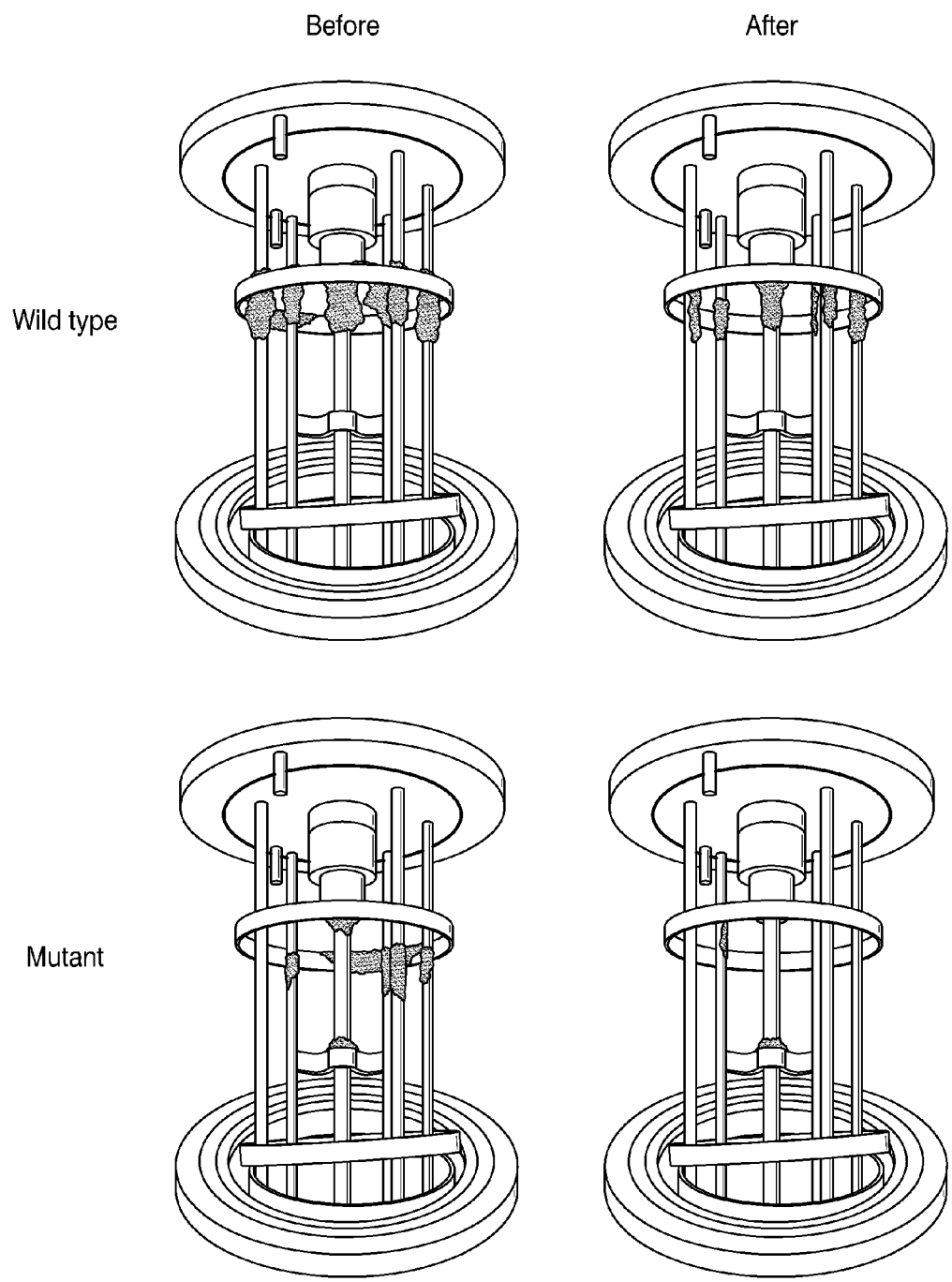
FIG. 3 shows the bioreactor hardware prior to and after the cleaning step. Wild type (left), hydrophobin mutant, delta 128530 (right).

At the end of the photographs of the bioreactors was taken. A "cleaning" step was included to elucidate the biomass adhesiveness. This step consisted of increasing the stirrer speed to 1000 RPM for 5 mins. The results can be found in FIG. 3.

REFERENCES

U.S. Pat. No. 7,338,779

Nielsen, M. L., L. Albertsen, G. Lettier, J. B. Nielsen and U. H. Mortensen (2006). "Efficient PCR-based gene targeting with a recyclable marker for *Aspergillus nidulans*." Fungal Genet Biol 43(1): 54-64.

Regueira T B, Kildegaard K R, Hansen B G, Mortensen U H, Hertweck C, Nielsen J. (2011) "Molecular basis for mycophenolic acid biosynthesis in *Penicillium brevicompactum*" Appl Environ Microbiol. May; 77(9):3035-43. Epub 2011 Mar. 11.

Kwan A H, Winefield R D, Sunde M, Matthews J M, Haverkamp R G, Templeton M D, Mackay J P. (2006) "Structural basis for rodlet assembly in fungal hydrophobins" PNAS vol 103, no. 10, page 3621-3626.

Linder M B, Szilvay G R, Nakari-Setälä T, Penttilä M E. (2005) "Hydrophobins: the protein-amphiphiles of filamentous fungi." FEMS Microbiol Rev. November; 29(5): 877-96. Epub 2005 Feb. 21.

The invention claimed is:

1. A filamentous fungus comprising a genetic modification in at least one hydrophobin gene, wherein said at least one hydrophobin gene encodes a polypeptide comprising an amino acid sequence selected from the group consisting of: the amino acid sequence having the sequence set forth in SEQ ID #1, an amino acid sequence having at least 85% sequence identity to SEQ ID #1, the amino acid sequence having the sequence set forth in SEQ ID #7, an amino acid sequence having at least 85% sequence identity to SEQ ID #7, the amino acid sequence set forth in SEQ ID #4 and an amino acid sequence having at least 85% sequence identity to SEQ ID #4, wherein said genetic modification reduces or abolishes the activity or expression of said hydrophobin, wherein said fungus is an *Aspergillus* spp and with the proviso that not all hydrophobin genes of said fungus are genetically modified, wherein said fungus further comprises at least one transgene, and wherein said transgene is encoded by an expression vector adapted for expression of said transgene.

2. The filamentous fungus of claim 1, wherein said at least one hydrophobin gene is deleted, partly deleted, disrupted by insertion of a DNA element or mutated in at least one nucleotide position.

3. The filamentous fungus according to claim 1, wherein expression of said at least hydrophobin gene is absent or, wherein the activity or expression of said at least one hydrophobin gene is reduced to 50% or less of the activity or the expression of said hydrophobin in said filamentous fungus with no genetic modification.

4. The filamentous fungus according to claim 1, wherein said fungus is an *Aspergillus* species selected from the group consisting of *Aspergillus niger*, *Aspergillus oryzae*, and *Aspergillus terreus*.

5. The filamentous fungus according to claim 1, wherein said at least one hydrophobin gene encodes a polypeptide comprising an amino acid sequence selected from the group consisting of: SEQ ID #1, an amino acid sequence having at least 85% sequence identity to SEQ ID #1, SEQ ID #7 and an amino acid sequence having at least 85% sequence identity to SEQ ID #7.

6. The filamentous fungus according to claim 1, wherein said at least one hydrophobin gene comprises the amino acid sequence set forth in SEQ ID #4 or an amino acid sequence having at least 85% sequence identity to SEQ ID #4.

7. The filamentous fungus according to claim 1 comprising a genetic modification in at least two hydrophobin genes, wherein said modifications reduce or abolish the activity or expression of said hydrophobins.

8. The filamentous fungus according to claim 7, wherein one of said two hydrophobin genes is a sequence encoding SEQ ID #1, or an amino acid sequence having at least 85% sequence identity to SEQ ID #1 and the second of said two hydrophobin gene is a sequence encoding SEQ ID #7 or an amino acid sequence having at least 85% sequence identity to SEQ ID #7.

9. A method for preparing a biosynthetic product comprising:
(i) providing a filamentous fungus according to claim 1;
(ii) culturing the fungus of step (i) under suitable conditions;
(iii) harvesting said biosynthetic product from the culture of step.

10. The method according to claim 9, wherein said biosynthetic product is selected from the group consisting of peptide, proteins, vitamins, enzymes, lipids, (poly)saccharides, nucleosides, biosynthetical drugs and antibiotics.

* * * * *

SEQUENCE LISTING

<160> NUMBER OF SEQ ID NOS: 9

<210> SEQ ID NO 1
<211> LENGTH: 105
<212> TYPE: PRT
<213> ORGANISM: Aspergillus niger

<400> SEQUENCE: 1

```
Gly Asn Ser Gln Val Arg Phe Pro Val Pro Gly Asp Met Thr Val Lys
1               5                   10                  15

Gln Ala Glu Asp Lys Cys Gly Asp Gln Ala Gln Leu Ser Cys Cys Asn
            20                  25                  30

Lys Ala Thr Tyr Ala Gly Asp Ser Thr Asn Val Asp Ser Gly Leu Leu
                35                  40                  45

Ala Gly Thr Leu Ser Asn Leu Ile Gly Thr Gly Ser Gly Ser Glu Gly
        50                  55                  60

Leu Gly Leu Phe Gln Glu Cys Ser Lys Leu Pro Ile Gln Ile Pro Ile
65                  70                  75                  80

Ile Gly Ile Ala Val Gln Asp Ile Ile Ser Lys Gln Cys Gln Gln Asn
                85                  90                  95

Ile Ala Cys Cys Gln Ser Ser Pro Ser
            100                 105

<210> SEQ ID NO 2
<211> LENGTH: 315
<212> TYPE: DNA
<213> ORGANISM: Aspergillus niger

<400> SEQUENCE: 2
ggcaacagcc aagttcgctt ccccgtcccc ggcgacatga ctgtcaagca ggccgaagac      60
aagtgcggtg accaggctca gctgtcctgc tgcaacaagg ccacctacgc tggtgacagc     120
accaacgttg acagcggtct cctcgctggt accctgtcca acctcattgg tactggatct     180
ggctccgagg gtctgggtct cttccaggag tgctccaagc tccctatcca gatccccatc     240
atcgggatcg ccgtccagga catcatcagc aagcagtgcc agcagaacat tgcttgctgc     300
cagtcgtctc cctct                                                      315

<210> SEQ ID NO 3
<211> LENGTH: 364
<212> TYPE: DNA
<213> ORGANISM: Aspergillus niger

<400> SEQUENCE: 3
ggcaacagcc aagttcgctt ccccgtcccc ggcgacatga ctgtcaagca ggccgaagac      60
aagtgcggtg accaggctca gctgtcctgc tgcaacaagg ccacctacgc tggtgacagc     120
accaacgttg acagcggtct cctcgctggt accctgtcca acctcattgg tactggatct     180
ggctccgagg gtctgggtct cttccaggag tgctccaagc tccctatcca gagtaagtct     240
tttccaacaa tcacaccaac ttacagtgct aattgttata gtccccatca tcgggatcgc     300
cgtccaggac atcatcagca agcagtgcca gcagaacatt gcttgctgcc agtcgtctcc     360
ctct                                                                  364

<210> SEQ ID NO 4
<211> LENGTH: 124
<212> TYPE: PRT
<213> ORGANISM: Aspergillus niger

<400> SEQUENCE: 4

Met Pro Gly Gly Ser Pro Ser Thr Gly Asn Gly Ala Gly Asn Gly Asn
1               5                   10                  15

Gly Asn Asp Gly Asn Ser Gln Val Arg Phe Pro Val Pro Gly Asp Met
            20                  25                  30

Thr Val Lys Gln Ala Glu Asp Lys Cys Gly Asp Gln Ala Gln Leu Ser
        35                  40                  45
```

```
Cys Cys Asn Lys Ala Thr Tyr Ala Gly Asp Ser Thr Asn Val Asp Ser
 50                  55                  60

Gly Leu Leu Ala Gly Thr Leu Ser Asn Leu Ile Gly Thr Gly Ser Gly
 65                  70                  75                  80

Ser Glu Gly Leu Gly Leu Phe Gln Glu Cys Ser Lys Leu Pro Ile Gln
                 85                  90                  95

Ile Pro Ile Ile Gly Ile Ala Val Gln Asp Ile Ile Ser Lys Gln Cys
            100                 105                 110

Gln Gln Asn Ile Ala Cys Cys Gln Ser Ser Pro Ser
        115                 120
```

<210> SEQ ID NO 5
<211> LENGTH: 372
<212> TYPE: DNA
<213> ORGANISM: Aspergillus niger

<400> SEQUENCE: 5

```
atgcccggtg gctctccttc cactggtaac ggtgccggca atggtaacgg caacgatggc    60
aacagccaag ttcgcttccc cgtccccggc gacatgactg tcaagcaggc cgaagacaag   120
tgcggtgacc aggctcagct gtcctgctgc aacaaggcca cctacgctgg tgacagcacc   180
aacgttgaca gcggtctcct cgctggtacc ctgtccaacc tcattggtac tggatctggc   240
tccgagggtc tgggtctctt ccaggagtgc tccaagctcc ctatccagat ccccatcatc   300
gggatcgccg tccaggacat catcagcaag cagtgccagc agaacattgc ttgctgccag   360
tcgtctccct ct                                                      372
```

<210> SEQ ID NO 6
<211> LENGTH: 420
<212> TYPE: DNA
<213> ORGANISM: Aspergillus niger

<400> SEQUENCE: 6

```
atgcccggtg gctctccttc cactggtaac ggtgccggca atggtaacgg caacgatggc    60
aacagccaag ttcgcttccc cgtccccggc gacatgactg tcaagcaggc cgaagacaag   120
tgcggtgacc aggctcagct gtcctgctgc aacaaggcca cctacgctgg tgacagcacc   180
aacgttgaca gcggtctcct cgctggtacc ctgtccaacc tcattggtac tggatctggc   240
tccgagggtc tgggtctctt ccaggagtgc tccaagctcc ctatccagag taagtctttt   300
ccaacaatca caccaactta cagtgctaat tgttatagtc cccatcatcg ggatcgccgt   360
ccaggacatc atcagcaagc agtgccagca gaacattgct tgctgccagt cgtctccctc   420
```

<210> SEQ ID NO 7
<211> LENGTH: 131
<212> TYPE: PRT
<213> ORGANISM: Aspergillus niger

<400> SEQUENCE: 7

```
Met Gln Phe Thr Leu Thr Asn Val Leu Ala Leu Thr Leu Ala Val Ala
  1               5                  10                  15

Thr Gly Val Ser Ala Gly Ala Val Ser Asp Ser Gln Ala Ile Lys Thr
                 20                  25                  30

Gln Thr Glu Gly Lys Cys Asp Ile Gly Asn Val Ser Cys Cys Asn Pro
             35                  40                  45

Thr Asn Glu Asp Lys Thr Asp Gly Phe Leu Asn Asn Leu Leu Glu Trp
 50                  55                  60
```

```
Gly Val Ile Gly Ser Leu Val Asn Gly Gln Gly Ser Ala Cys Ala Pro
 65              70                  75                  80

Ile Ser Leu Ile Asp Glu Leu Gly Ile Leu Ala Leu Val Lys Asp Thr
                 85                  90                  95

Pro Asp Gly Pro Val Cys Glu Asn Val Ile Ala Cys Cys Pro Gly Gln
            100                 105                 110

Gly Ala Gln Cys Val Ala Ile Gly Asp Gly Ser Gly Ser Gly Ser Gly
        115                 120                 125

Tyr Ser Asp
    130
```

```
<210> SEQ ID NO 8
<211> LENGTH: 396
<212> TYPE: DNA
<213> ORGANISM: Aspergillus niger

<400> SEQUENCE: 8
atgcagttca ctctcaccaa cgttcttgcc ctcaccctcg cggtcgccac cggcgtctct      60
gctggcgctg tctctgactc ccaagccatt aagacccaga ctgagggcaa gtgcgatatt     120
ggcaacgtct cgtgctgcaa cccaaccaac gaggacaaga ctgatggctt cctcaacaac     180
ctgctcgagt ggggtgttat cggcagtctg gtcaacggtc agggatccgc ttgcgctccg     240
atcagcctca ttgatgagct tggaattctg gccctcgtca aggatacccc tgatggaccg     300
gtctgcgaaa atgtcattgc ttgctgccct ggtcagggtg ctcagtgtgt cgccatcggt     360
gacggctctg gctccggctc cggctacagc gactaa                               396

<210> SEQ ID NO 9
<211> LENGTH: 571
<212> TYPE: DNA
<213> ORGANISM: Aspergillus niger

<400> SEQUENCE: 9
atgcagttca ctctcaccaa cgttcttgcc ctcaccctcg cggtcgccac cggcgtctct      60
gctggcgctg tctctgactc ccaagccatt aagacccaga ctgagggcaa gtgcgatatt     120
ggcaacgtct cgtgctgcaa cccaaccaac gaggacaaga ctgatggctt cctcaacaac     180
ctgctcgagt ggggtgttat cggcagtctg gtcaacggtc agggatccgc ttgcgctccg     240
atcagcctca ttgatgagct tggaattctg gtatgattg atcctctaca tacagttttg     300
accttagctt tggaagatgt atcactgaca ttgatgaaat catgaaacag ccctcgtcaa     360
ggatacccct gatggaccgg tctgcgaaaa tgtcattgct tgctgccctg gtcagggtgc     420
tcaggtacgt ctgccttcta ttttcccttc caacttcata gattctgtcc ttttctgttt     480
caaatagatc cttaataact aacatgacta ttttttacag tgtgtcgcca tcggtgacgg     540
ctctggctcc ggctccggct acagcgacta a                                    571
```